(12) United States Patent
Tsuang et al.

(10) Patent No.: US 8,840,648 B2
(45) Date of Patent: Sep. 23, 2014

(54) SPINAL CAGE AND IMPLANTING METHOD THEREOF

(75) Inventors: Yang-Hwei Tsuang, Taipei (TW);
Chang Jung Chiang, Taichung (TW);
Shan-Chang Chueh, Taipei (TW);
Chun-Jen Liao, Taipei (TW);
Chung-Nun Chen, Taichung County (TW); Ya-Jen Yu, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 546 days.

(21) Appl. No.: 12/751,944

(22) Filed: Mar. 31, 2010

(65) Prior Publication Data

US 2010/0256764 A1 Oct. 7, 2010

(30) Foreign Application Priority Data

Apr. 1, 2009 (TW) .............................. 98110819 A
Mar. 24, 2010 (TW) .............................. 99108659 A

(51) Int. Cl.
*A61B 17/88* (2006.01)
*A61B 17/58* (2006.01)
*A61B 17/60* (2006.01)
*A61F 2/00* (2006.01)
*A61F 2/44* (2006.01)
*A61F 2/46* (2006.01)
*A61F 2/30* (2006.01)
*A61F 2/28* (2006.01)

(52) U.S. Cl.
CPC ......... *A61F 2/442* (2013.01); *A61F 2002/4623* (2013.01); *A61F 2002/4485* (2013.01); *A61F 2002/30579* (2013.01); *A61F 2/4611* (2013.01); *A61F 2002/4475* (2013.01); *A61F 2002/4628* (2013.01); *A61F 2002/448* (2013.01); *A61F 2002/2835* (2013.01); *A61F 2002/4629* (2013.01); *A61F 2310/00365* (2013.01); *A61F 2002/4627* (2013.01); *A61F 2310/00293* (2013.01); *A61F 2310/00383* (2013.01); *A61F 2002/3052* (2013.01); *A61F 2002/3055* (2013.01); *A61F 2310/00221* (2013.01); *A61F 2220/0025* (2013.01)
USPC ........................... 606/279; 606/99; 623/17.12

(58) Field of Classification Search
USPC ............ 623/17.11–17.16; 606/86 R, 99, 246, 606/279
See application file for complete search history.

(56) References Cited

U.S. PATENT DOCUMENTS 6,143,032 A  11/2000 Schafer et al.
6,245,108 B1  6/2001 Biscup
(Continued)

FOREIGN PATENT DOCUMENTS

CN  101014292  8/2007
CN  101288608  10/2008

OTHER PUBLICATIONS

Taiwan Patent Office, Office Action, Patent Application Serial No. 099108659, Jan. 30, 2012, Taiwan.

*Primary Examiner* — Andrew Yang
*Assistant Examiner* — Diana S Jones

(57) ABSTRACT

A spinal cage is provided to be implanted in an intervertebral disc space. The spinal cage includes a first segment and a second segment movably connected with each other. The first segment is slidable with respect to the second segment, so as to elongate the spinal cage from a retracted state to an extended state.

9 Claims, 25 Drawing Sheets

(56) References Cited

U.S. PATENT DOCUMENTS

| | | |
|---|---|---|
| 6,387,130 B1 | 5/2002 | Stone et al. |
| 6,599,294 B2 * | 7/2003 | Fuss et al. .................. 606/99 |
| 6,645,206 B1 | 11/2003 | Zdeblick et al. |
| 7,252,686 B2 * | 8/2007 | Carrison et al. ........... 623/17.16 |
| 7,850,734 B2 * | 12/2010 | Oh et al. .................... 623/17.16 |
| 8,021,429 B2 * | 9/2011 | Viker ......................... 623/17.16 |
| 2004/0127990 A1 | 7/2004 | Bartish, Jr. et al. |
| 2009/0030423 A1 * | 1/2009 | Puno .............................. 606/99 |

* cited by examiner

SPINAL CAGE AND IMPLANTING METHOD THEREOF

CROSS REFERENCE TO RELATED APPLICATIONS

This Application claims priority of Taiwan Patent Application No. 098110819 and No. 99108659, respectively filed on Apr. 1, 2009 and Mar. 24, 2010, the entirety of which is incorporated by reference herein.

BACKGROUND

1. Technical Field

The disclosure relates in general to a spinal cage and in particular to an extendable spinal cage and implanting method thereof.

2. Description of the Related Art

Referring to FIG. 1, the human spine 100 comprises a column of vertebrae 110 and adjoining structures. The bodies of the vertebrae 110 are connected by anterior and posterior ligaments and intervertebral disks 120. The column of vertebrae 110 and intervertebral disks 120 form a central axis that supports the head and torso of bodies.

One of the most costly health problems involves back pain and pathology of the spine. Back pain may be caused by several factors such as congenital deformities, traumatic injuries, degenerative changes to the spine and the likes. Additionally, herniation of intervertebral disc may lead to nerve conduction disorders. Upon identification of these abnormalities, spinal fusion surgery may be required to correct the problems.

Conventional spinal fusion can fix the vertebrae together by implanting a spinal cage P between the vertebrae 110, thus preventing movement therebetween and maintaining a space originally occupied by the intervertebral disk 120. However, since conventional spinal cages usually have considerable dimensions, large surgical sites are inevitable and adversely influence patients.

SUMMARY

An embodiment of the present disclosure provides a spinal cage to be implanted in an intervertebral disc space. The spinal cage includes a first segment and a second segment movably connected with each other. The first segment is slidable with respect to the second segment, so as to elongate the spinal cage from a retracted state to an extended state.

BRIEF DESCRIPTION OF DRAWINGS

The disclosure can be more fully understood by reading the subsequent detailed description and examples with references made to the accompanying drawings, wherein:

FIG. 8b is a large view of the portion A in FIG. 8a;

FIG. 10b is a large view of the portion B in FIG. 10a;

DETAILED DESCRIPTION OF EMBODIMENTS

Figure 1:
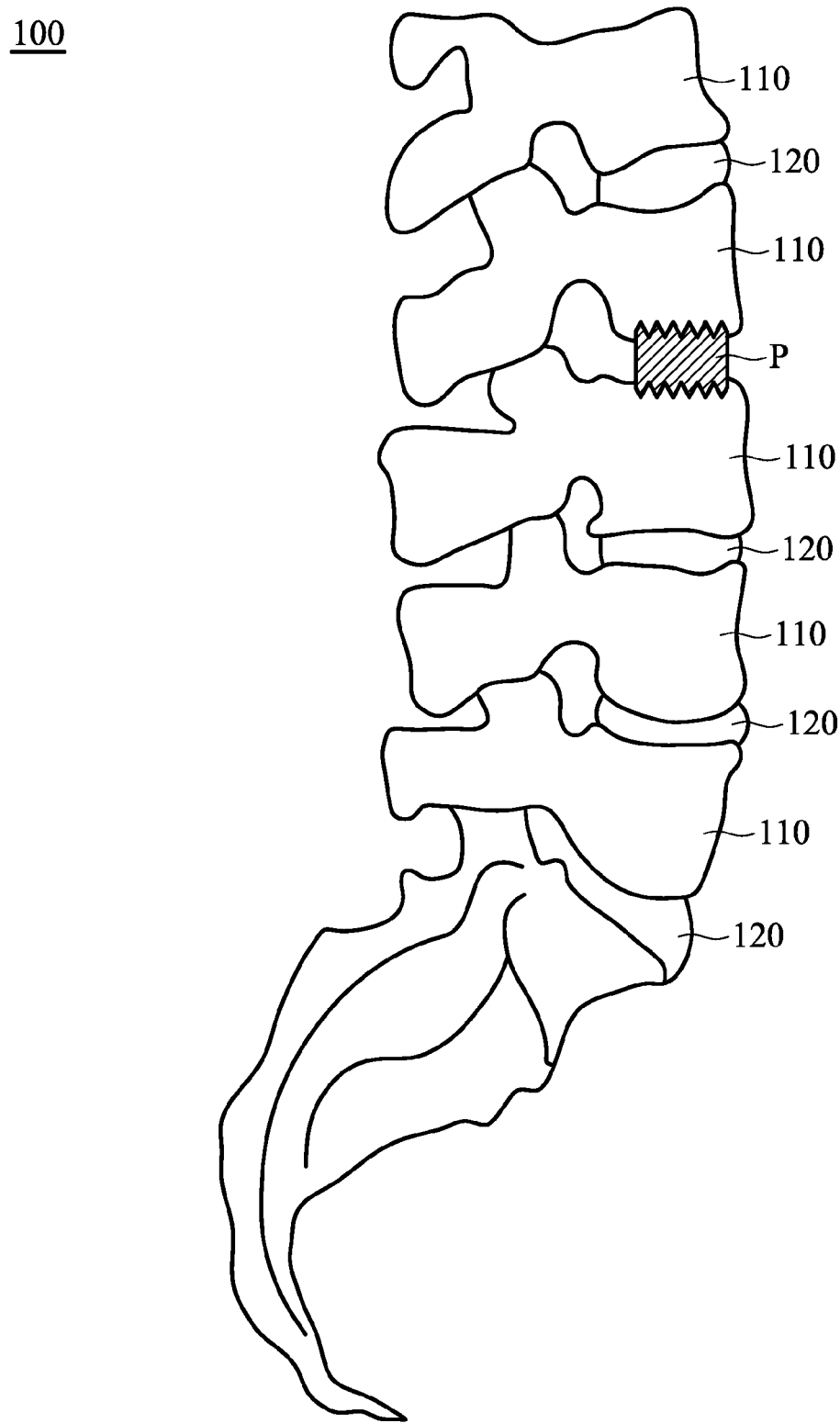
FIG. 1 is a perspective diagram of a conventional spinal cage implanted between the vertebrae.
Figure 2A:
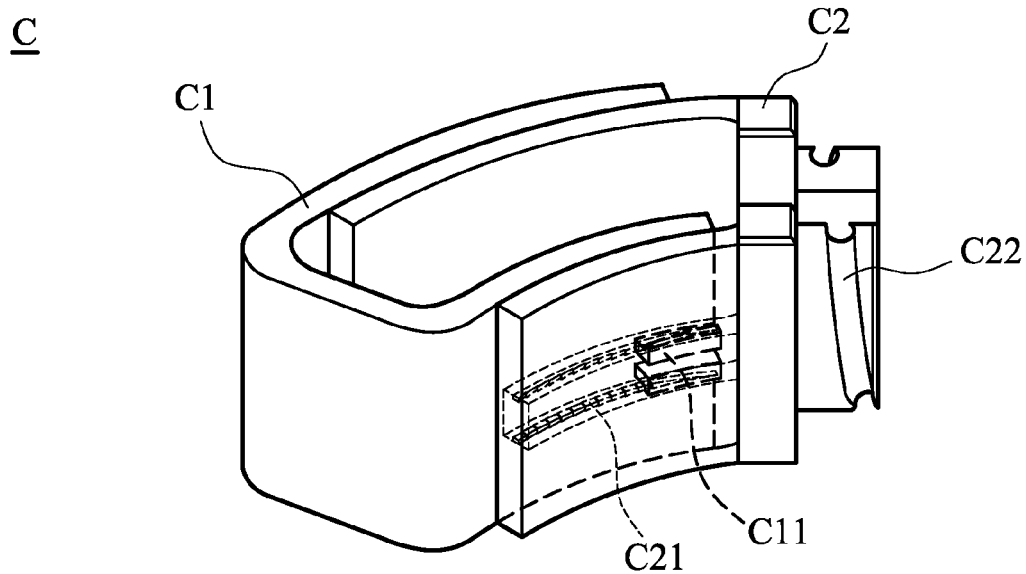
FIGS. 2a-2c are perspective diagrams of a spinal cage according to an embodiment of the disclosure.
Figure 2B:
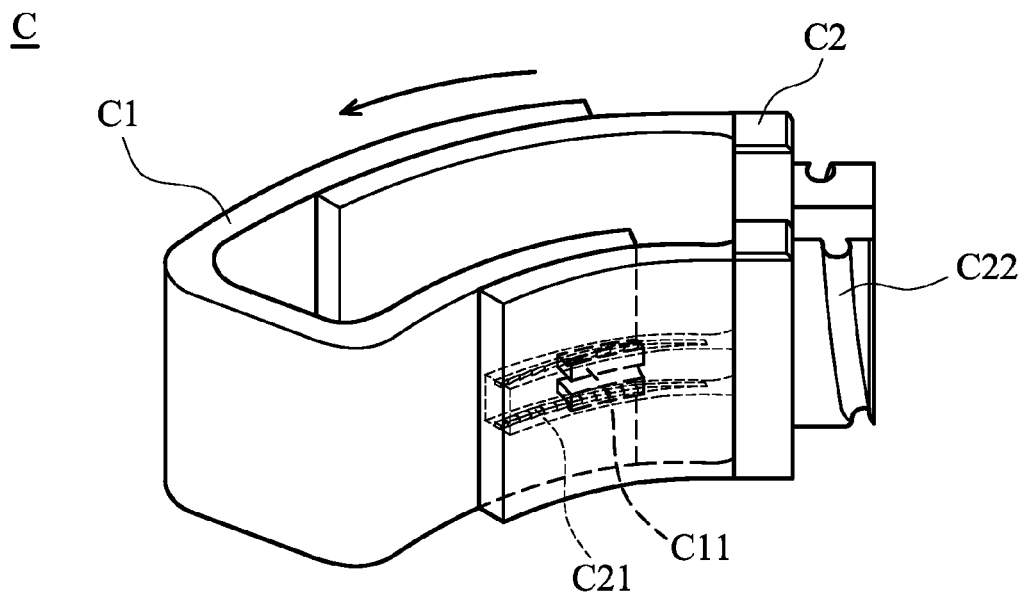
Figure 2C:
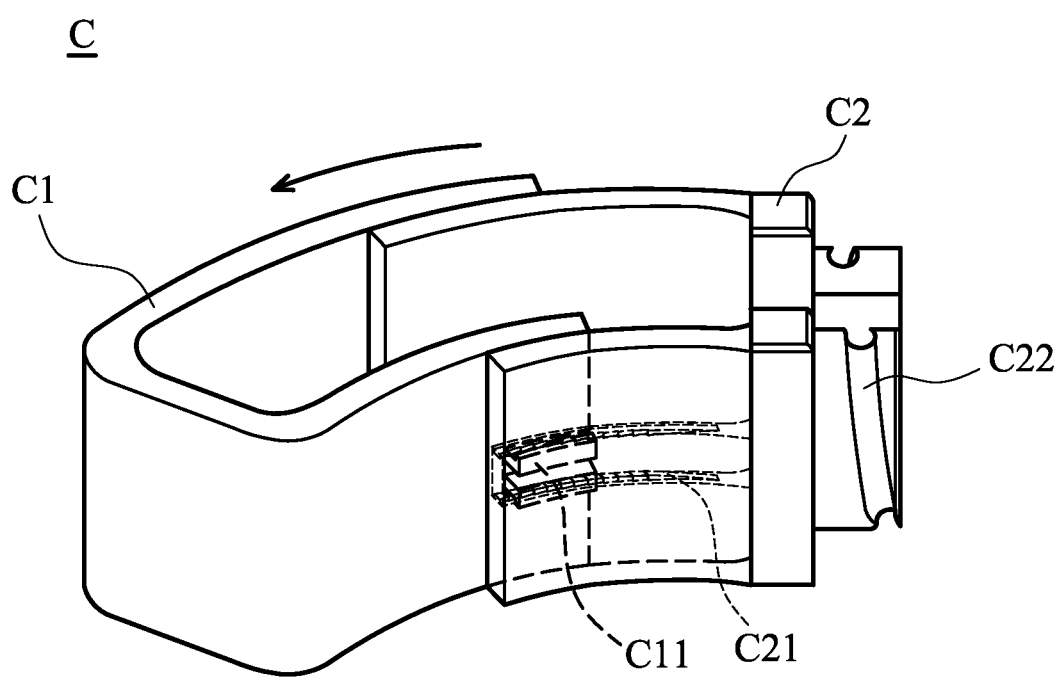

Referring to FIGS. 2a-2c, an embodiment of a spinal cage C is implanted in the intervertebral disc space to prevent nerve conduction disorders due to herniation thereof. The spinal cage C primarily comprises a first segment C1 and a second segment C2, and both of them have a hollow and curved structure. Specifically, the first segment C1 is slidable with respect to second segment C2. Before implanting the spinal cage C, as shown in FIG. 2a, the spinal cage C is in a retracted state with small dimensions and capable of being used in minimally invasive surgery.

When the spinal cage C is implanted into the intervertebral disc space, the first segment C1 is pushed by a rod and extended with respect to the second segment C2, as shown in FIG. 2b. With a slider C11 of the first segment C1 continuously sliding along a rail C21 of the second segment C2, the spinal cage C is elongated to an extended state, as shown in FIG. 2C. In this embodiment, the rail C21 has a ratchet structure to prevent retraction of the spinal cage C.

Figure 3A:
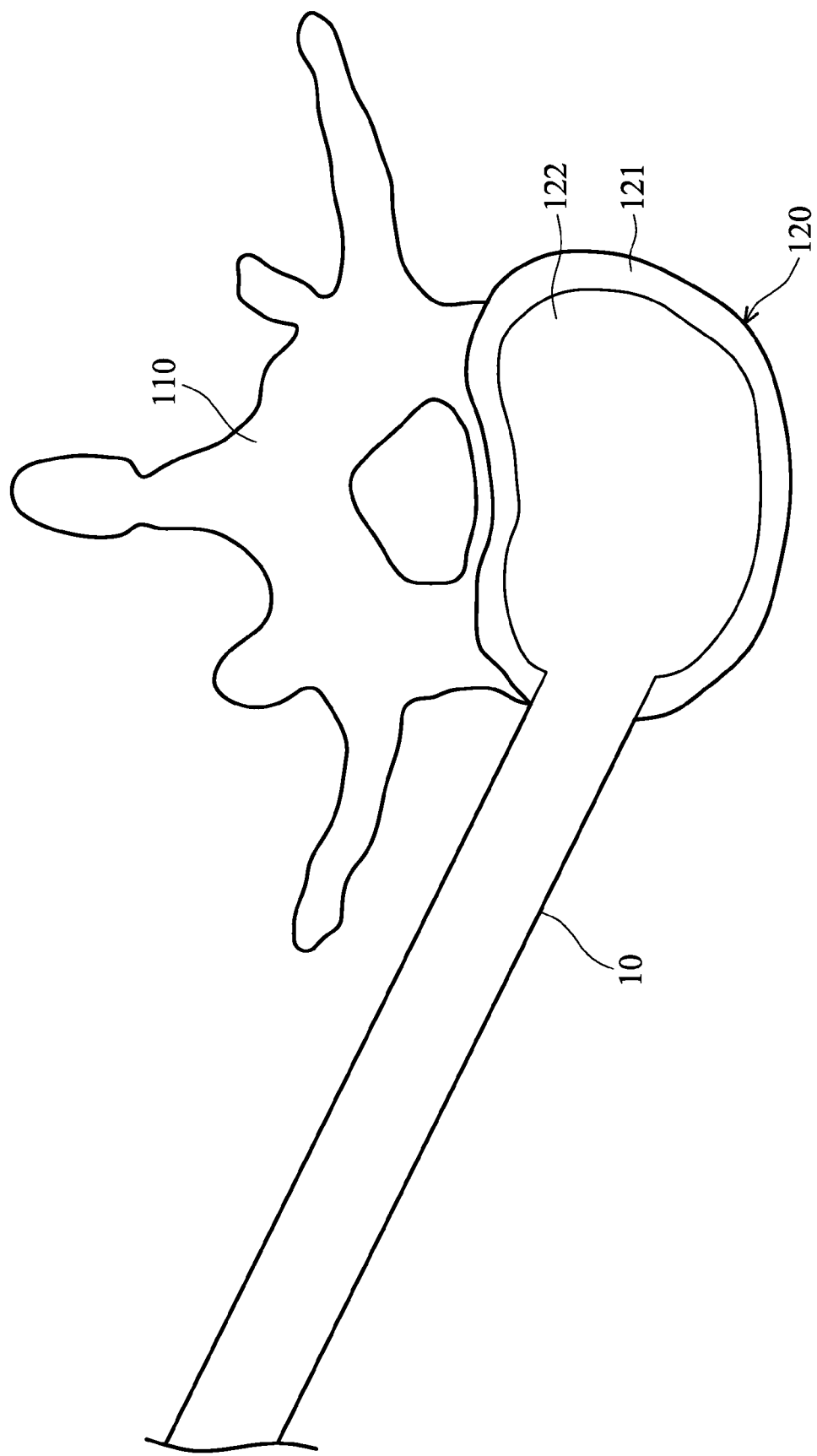
FIGS. 3a-3c, 4a-4d, 5, and 6a-6c are perspective diagrams illustrating a method for implanting a spinal cage into the intervertebral disc space.
Figure 3B:
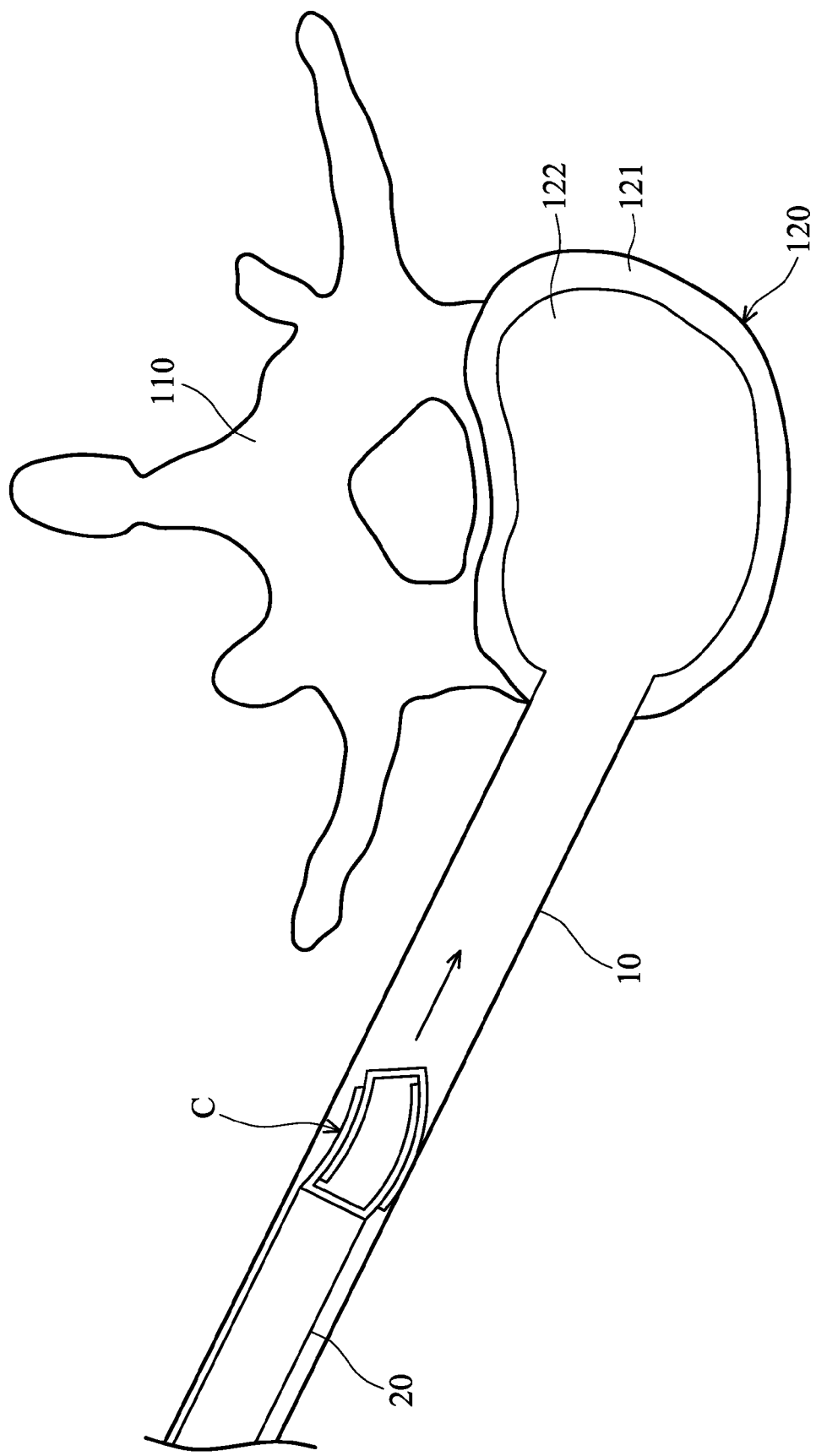
Figure 3C:
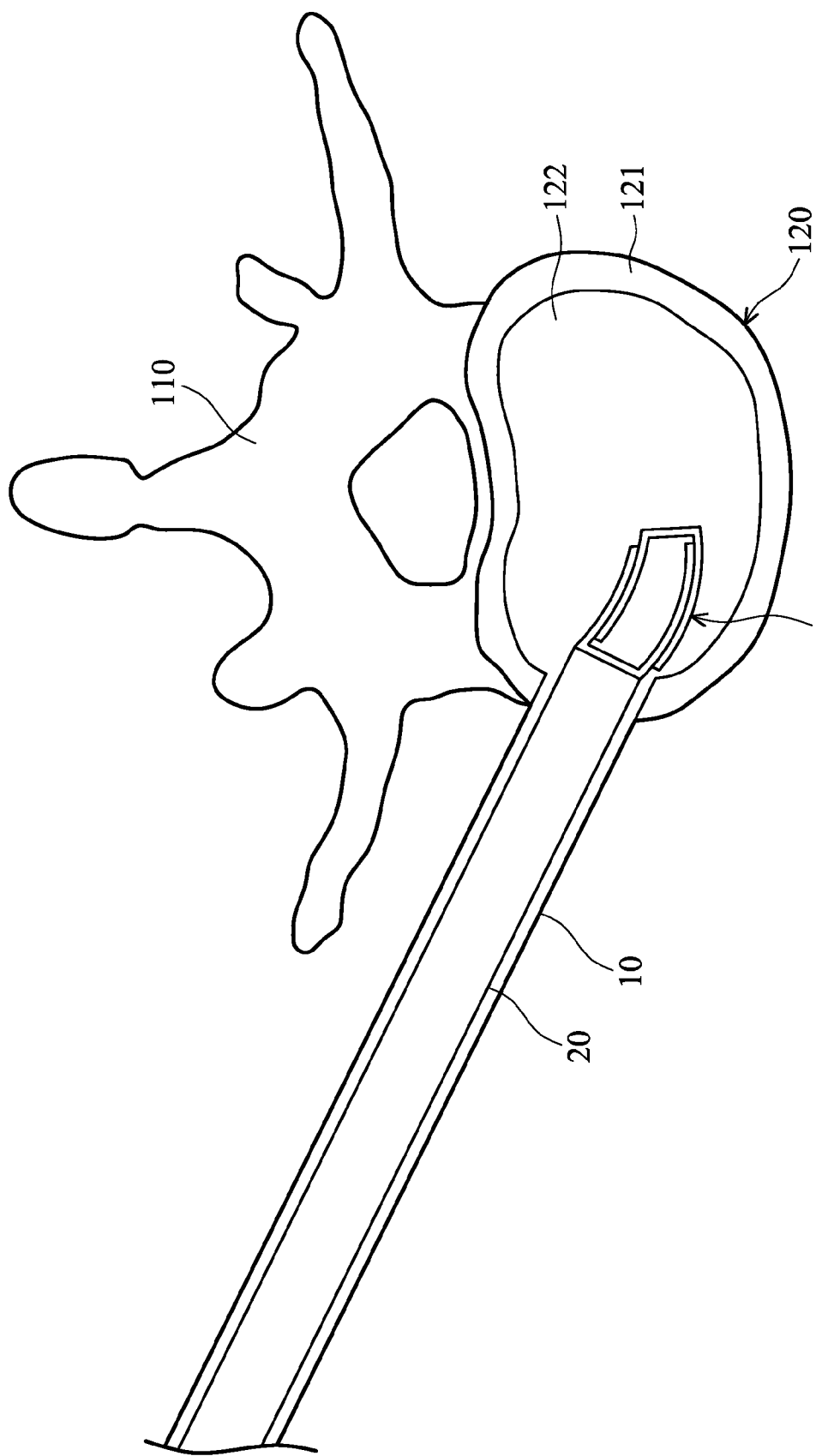

Referring to FIG. 3a, before implanting the spinal cage C, a pipe 10 penetrates the annulus fibrosus 121 of the intervertebral disc 120 to form a passage communicated with the nucleus pulposus 122 thereof. Subsequently, the retracted spinal cage C is delivered by a hollow tube 20 through the pipe 10 to the nucleus pulposus 122, as shown in FIGS. 3b and 3c.

Figure 4A:
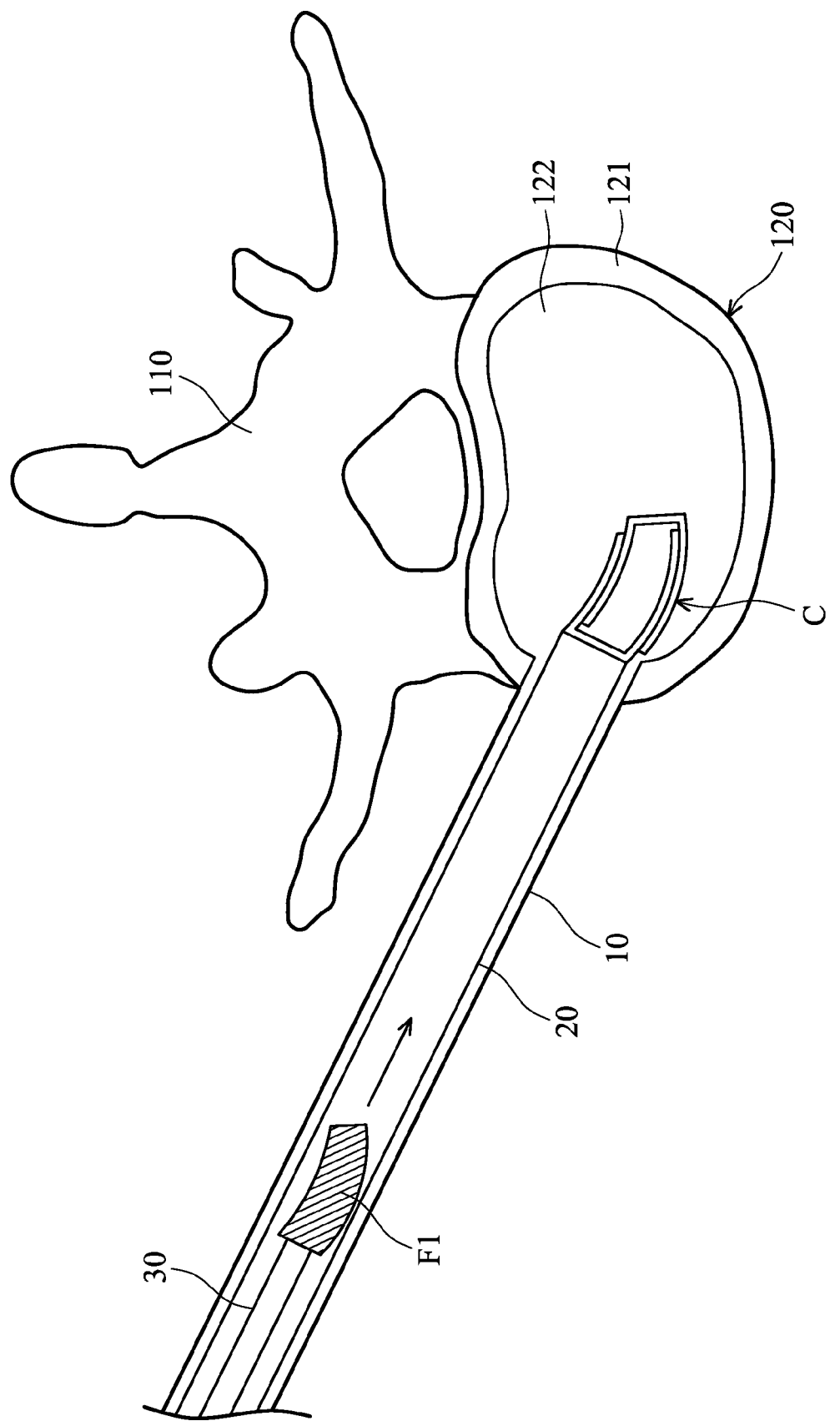
Figure 4B:
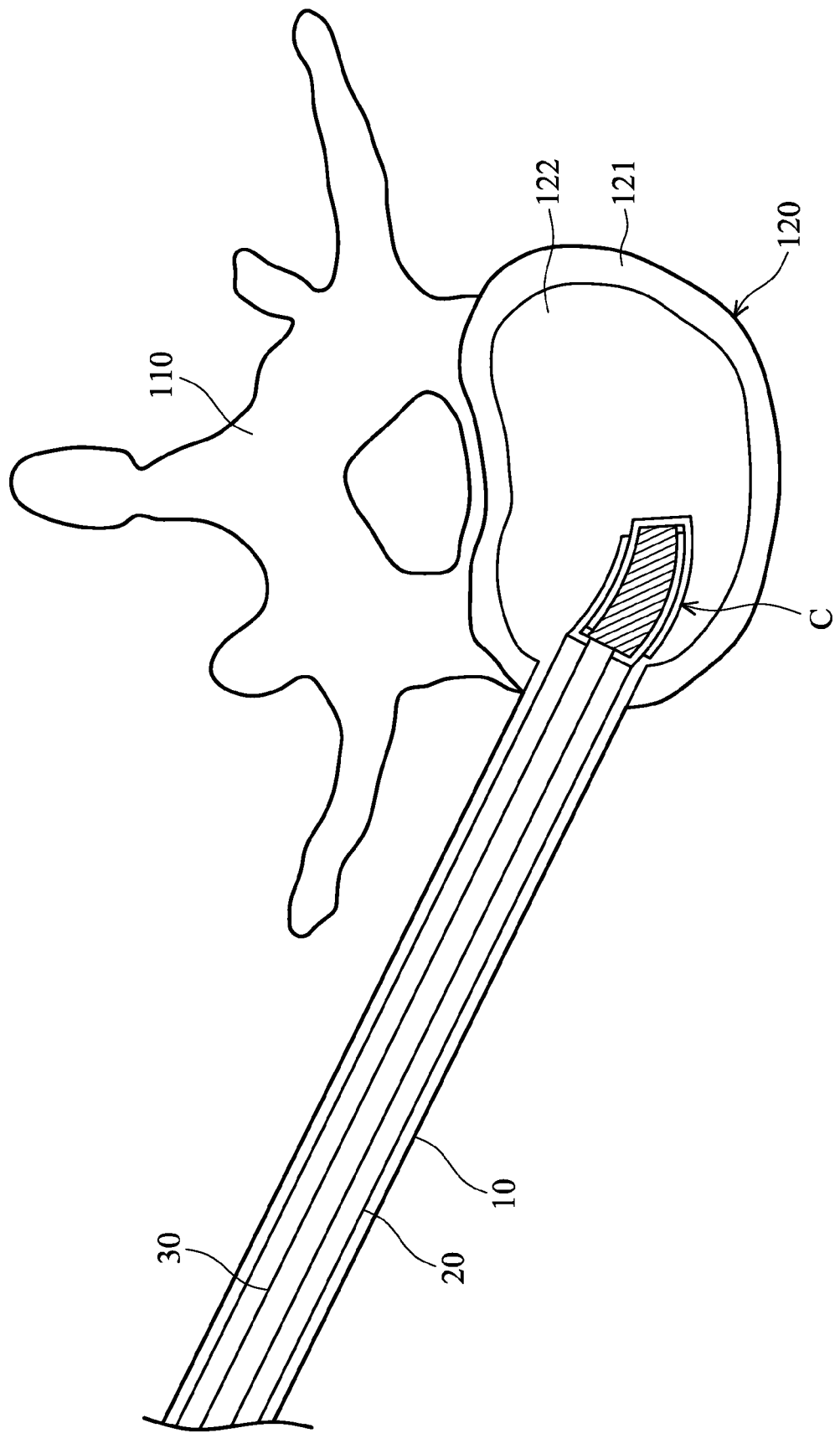
Figure 4C:
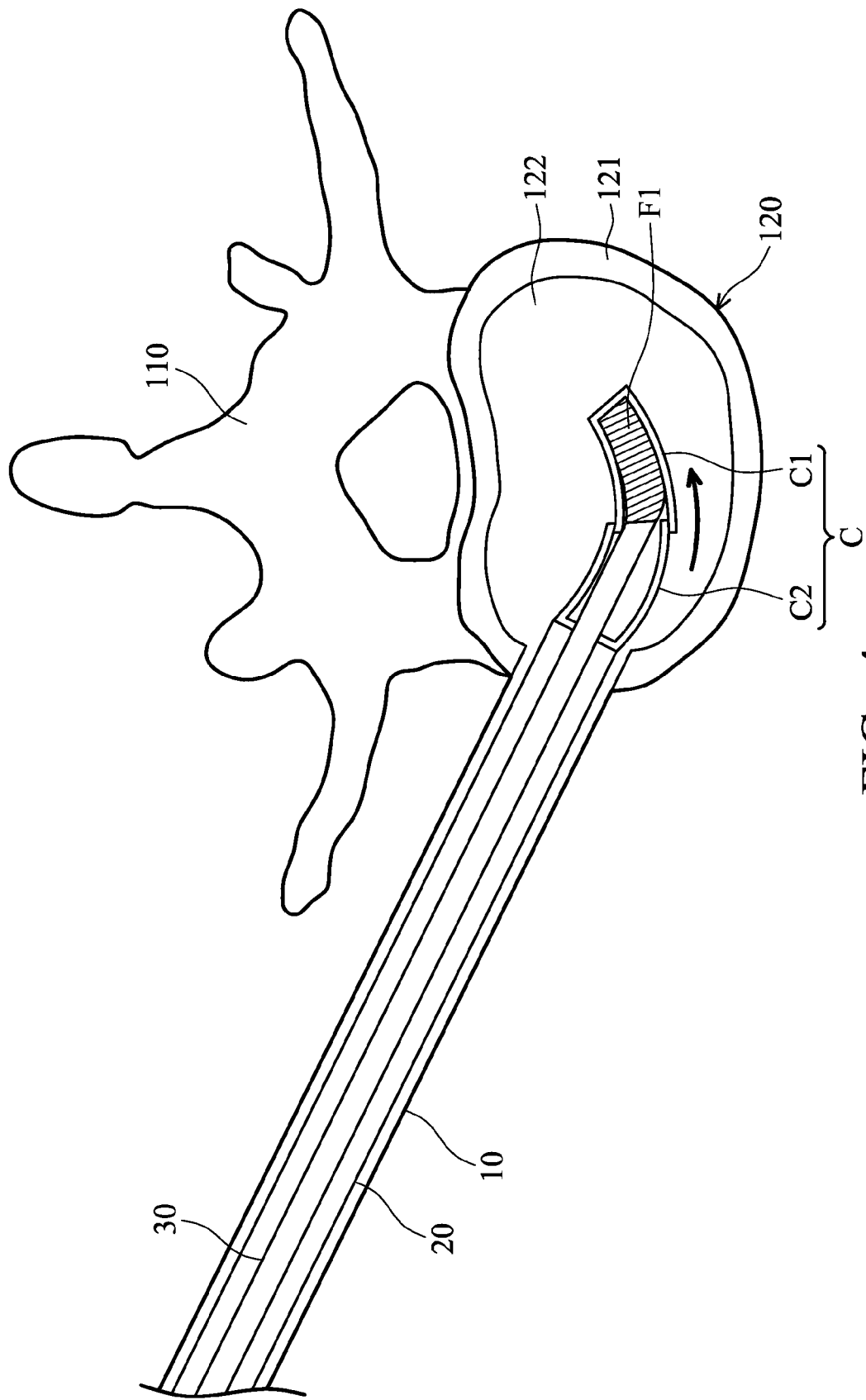
Figure 4D:
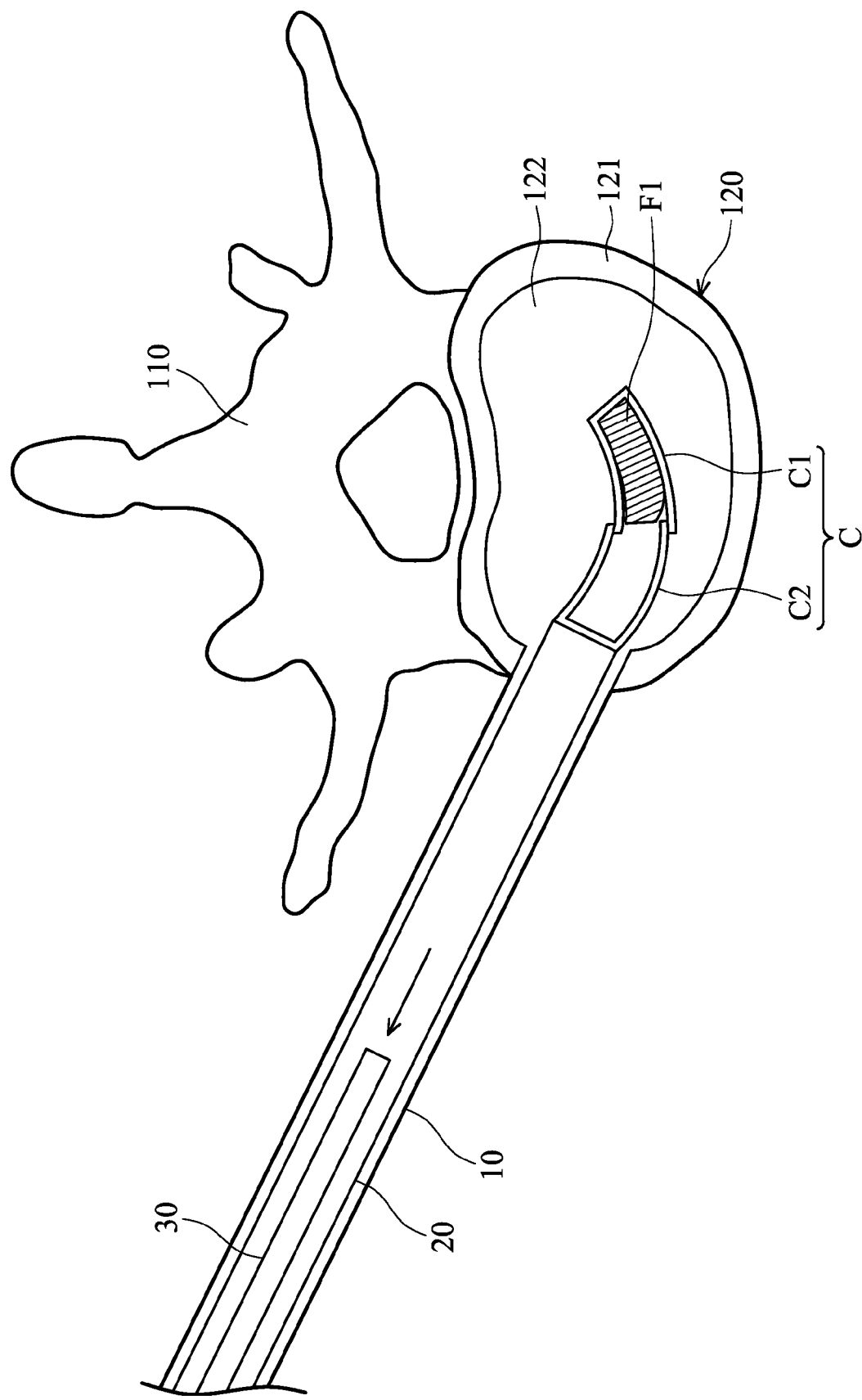

Referring to FIGS. 4a-4b, when the spinal cage C is moved into the intervertebral disc 120, filler F1 is delivered into the spinal cage C by a rod 30 through the hollow tube 20. With the rod 30 progressively moving forward, as the arrow indicates in FIG. 4c, the filler F1 pushes against the first segment C1 of the spinal cage C, so that the first segment C1 slides with respect to the second segment C2 to the right, and the spinal cage C is elongated to an extended state. The rod 30 is then drawn out of the tube 20 with the filler F1 received in the first segment C1, as shown in FIG. 4d.

Figure 5:
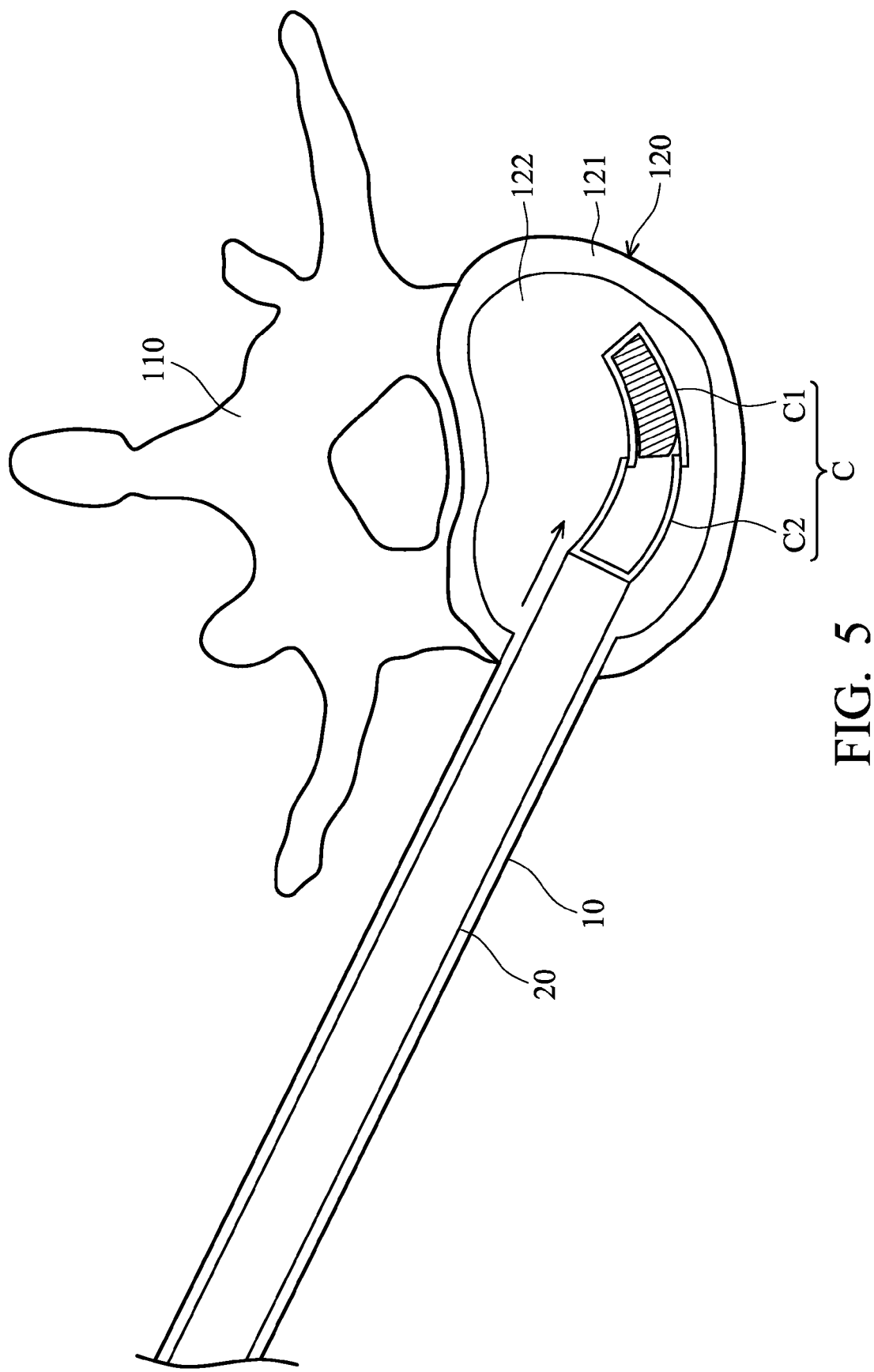
Figure 6A:
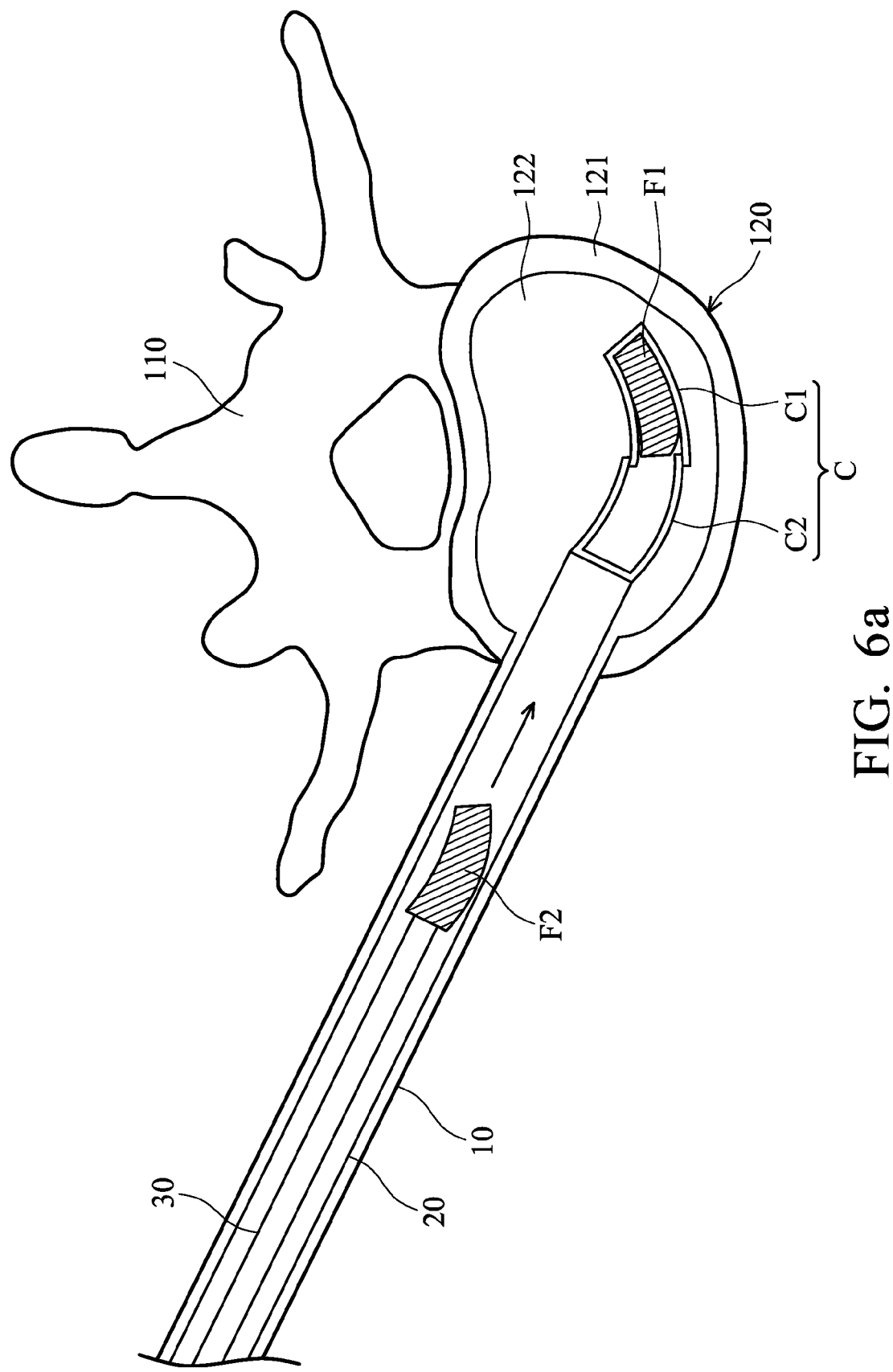
Figure 6B:
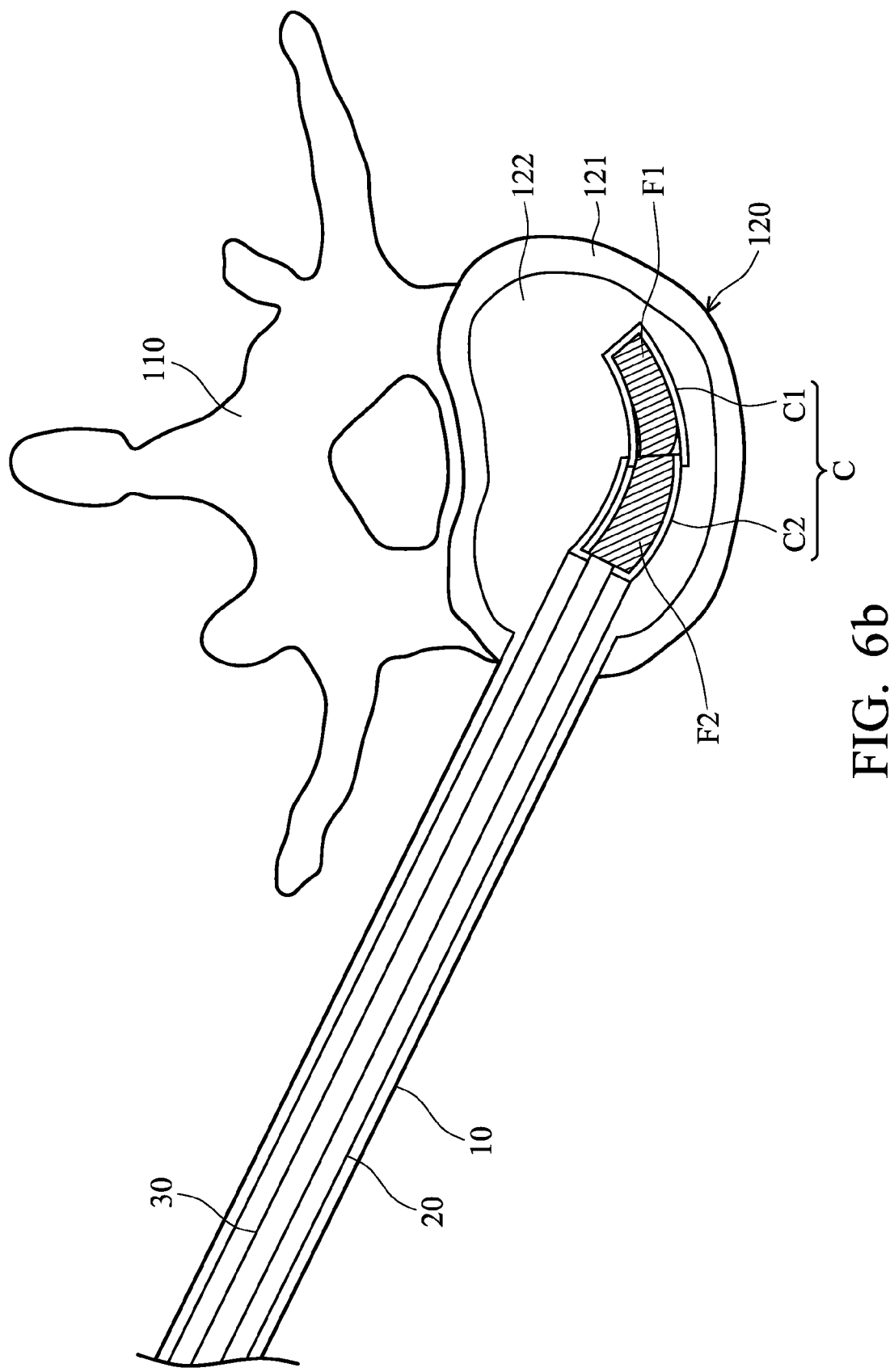
Figure 6C:
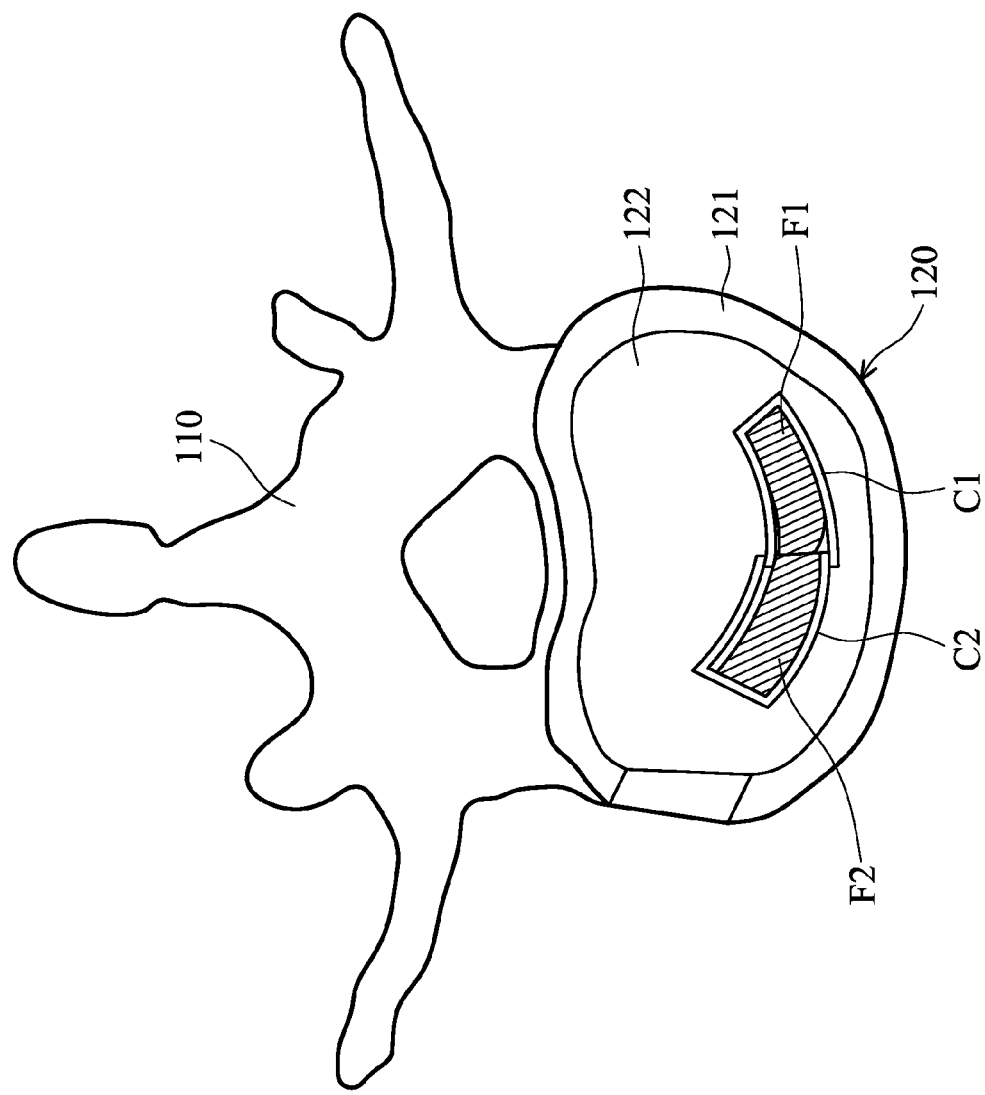

Referring to FIG. 5, when the spinal cage C is elongated to the extended state, the spinal cage C can be adjusted to a target position by precisely moving the tube 20, so as to provide robust structural support and connection between the vertebrae. In FIGS. 6a and 6b, another filler F2 is also delivered into the second segment C2 by the rod 30. The rod 30, the tube 20, and the pipe 10 are then sequentially drawn out of the human body, such that the spinal cage C is permanently left in the intervertebral disc 120, as shown in FIG. 6c.

In this embodiment, the filler F1 and F2 may comprise autologous tissue, allograft tissue, or porous artificial bone substitute such as hydroxyapatite (HAp), tricalcium phosphate, $CaSO_4$, $CaCO_3$, collagen, or gelatin.

As shown in FIGS. 2a-2c, the second segment C2 of the spinal cage C has an engaging portion, such as a threaded portion C22 detachably engaged with an end of the tube 20. Before drawing the tube 20 out of the human body, the tube 20 can be released from the threaded portion C22 by slightly rotating the tube 20 with respect to the spinal cage C. Hence, the spinal cage C is left in the intervertebral disc 120 safely and permanently.

Figure 7A:
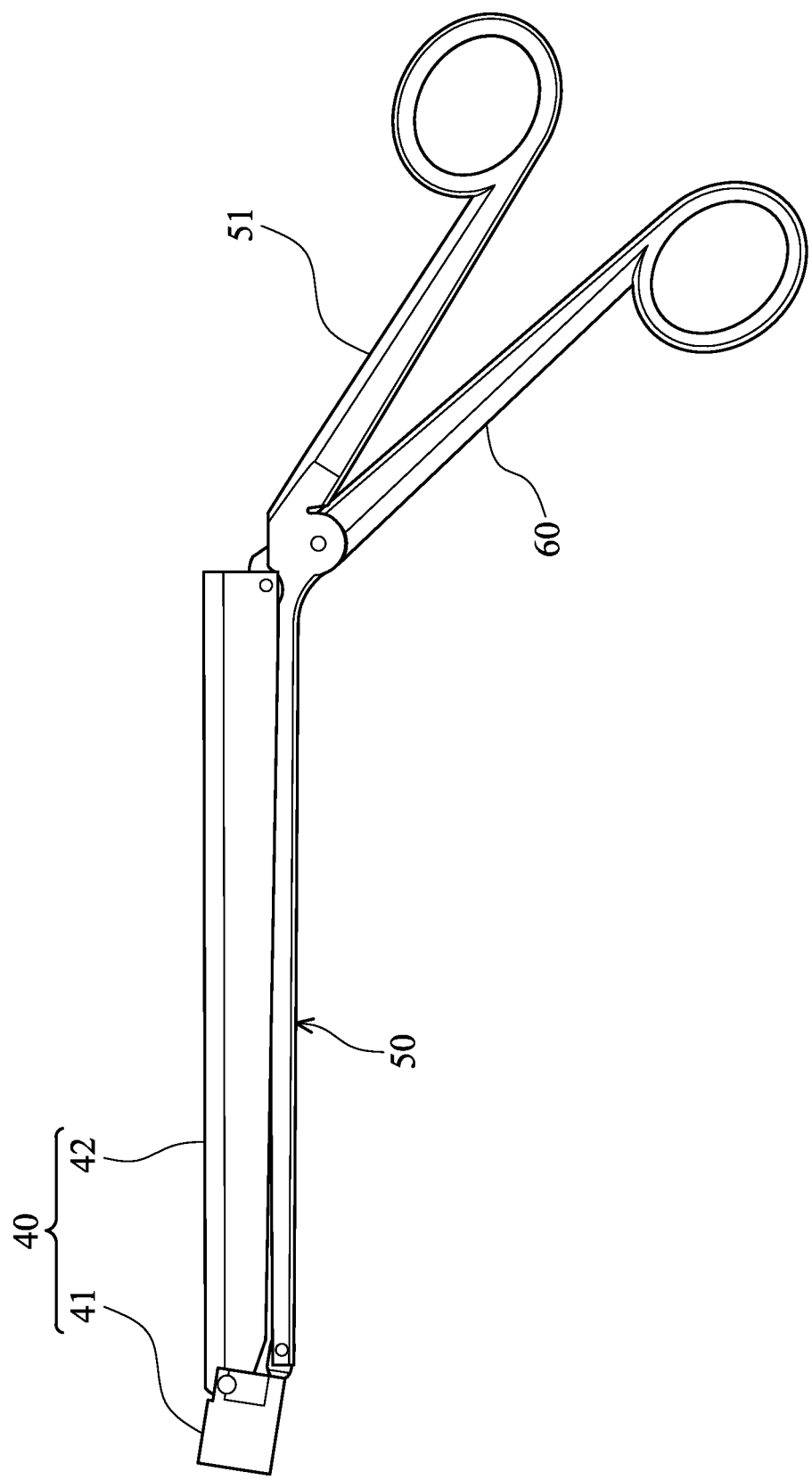
FIGS. 7a-7b are perspective diagrams of a guiding device according to an embodiment of the disclosure.
Figure 7B:
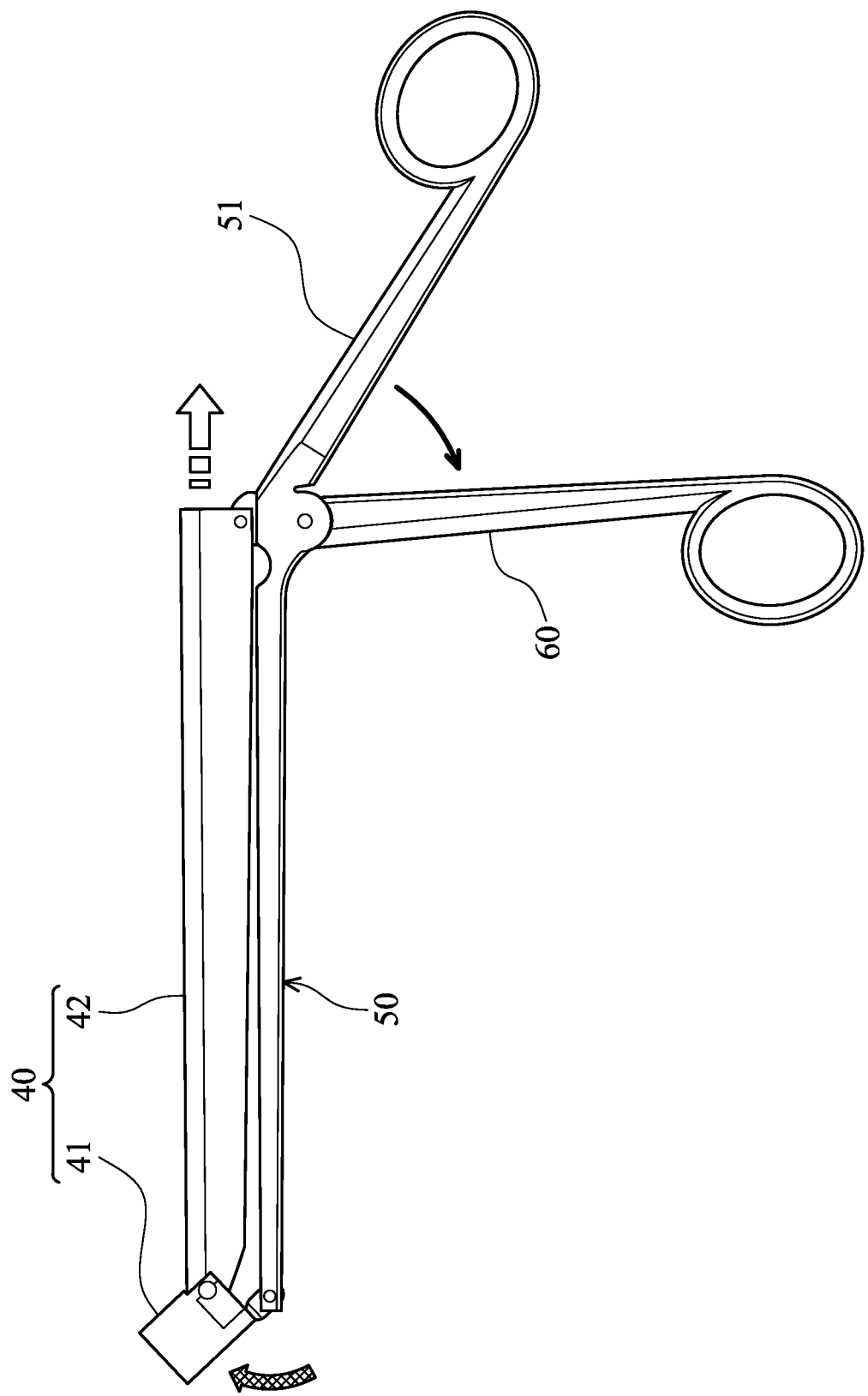

FIGS. 7a and 7b illustrate a guiding device for implanting the aforesaid spinal cage C into the intervertebral disc space. The guiding device comprises a hollow mechanism 40, an arm 50 and a handle 60. As shown in FIGS. 7a and 7b, the hollow mechanism 40 includes a first tube 41 and a second tube 42 which are pivotally connected to the arm 50 and the handle 60, wherein the arm 50 and the handle 60 form a scissors structure. When using the guiding device, an elevating angle of the first tube 41 can be adjusted by manually manipulating the arm 50 and the handle 60. When the angle between the arm 50 and the handle 60 is increased, the second tube 42 is moved to the right and the first tube 41 rotates upward, as the arrows indicate in FIG. 7b.

Figure 8A:
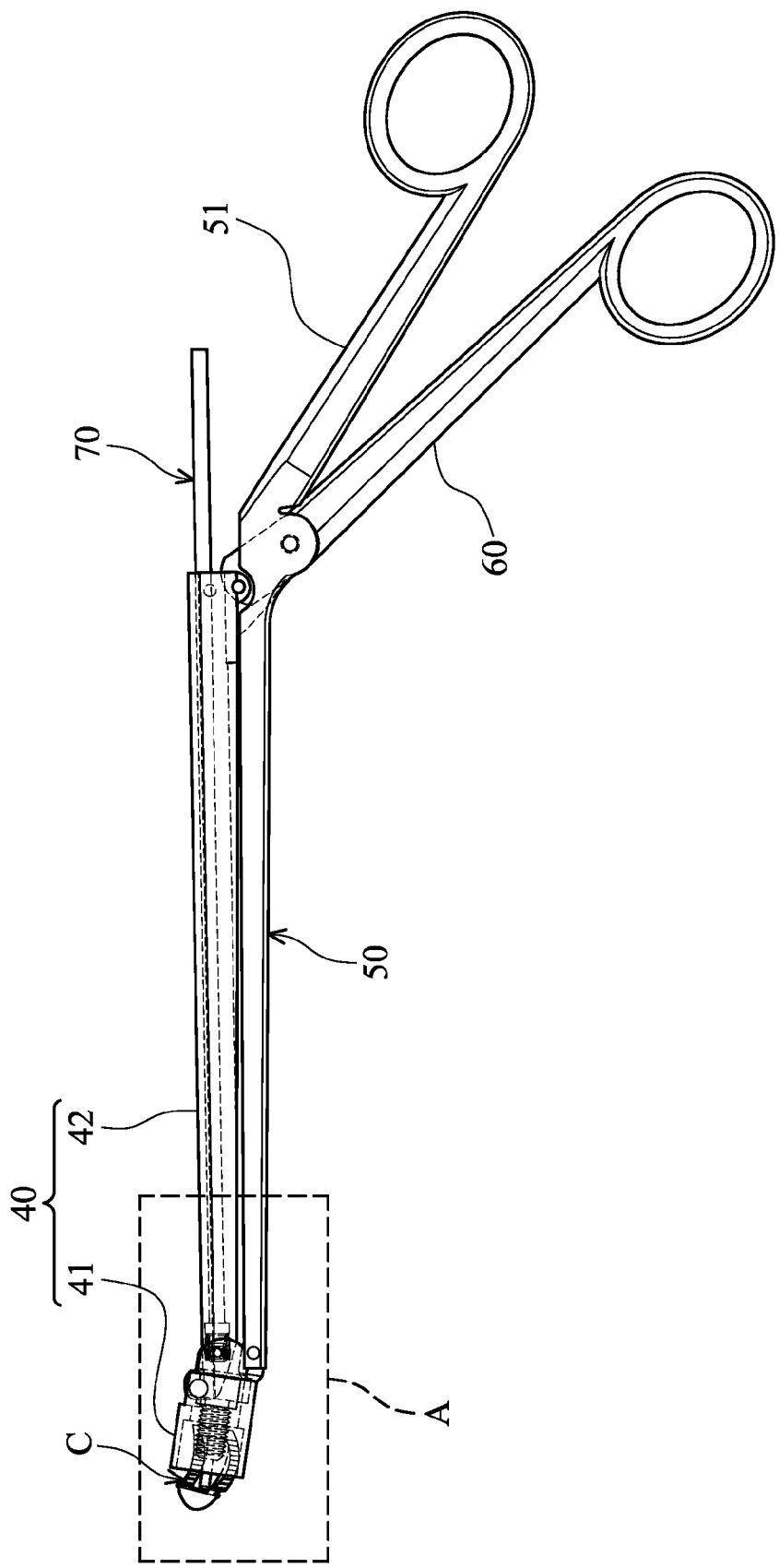
FIG. 8a is a perspective diagram of a pushing mechanism disposed through a guiding device according to an embodiment of the disclosure.
Figure 8B:
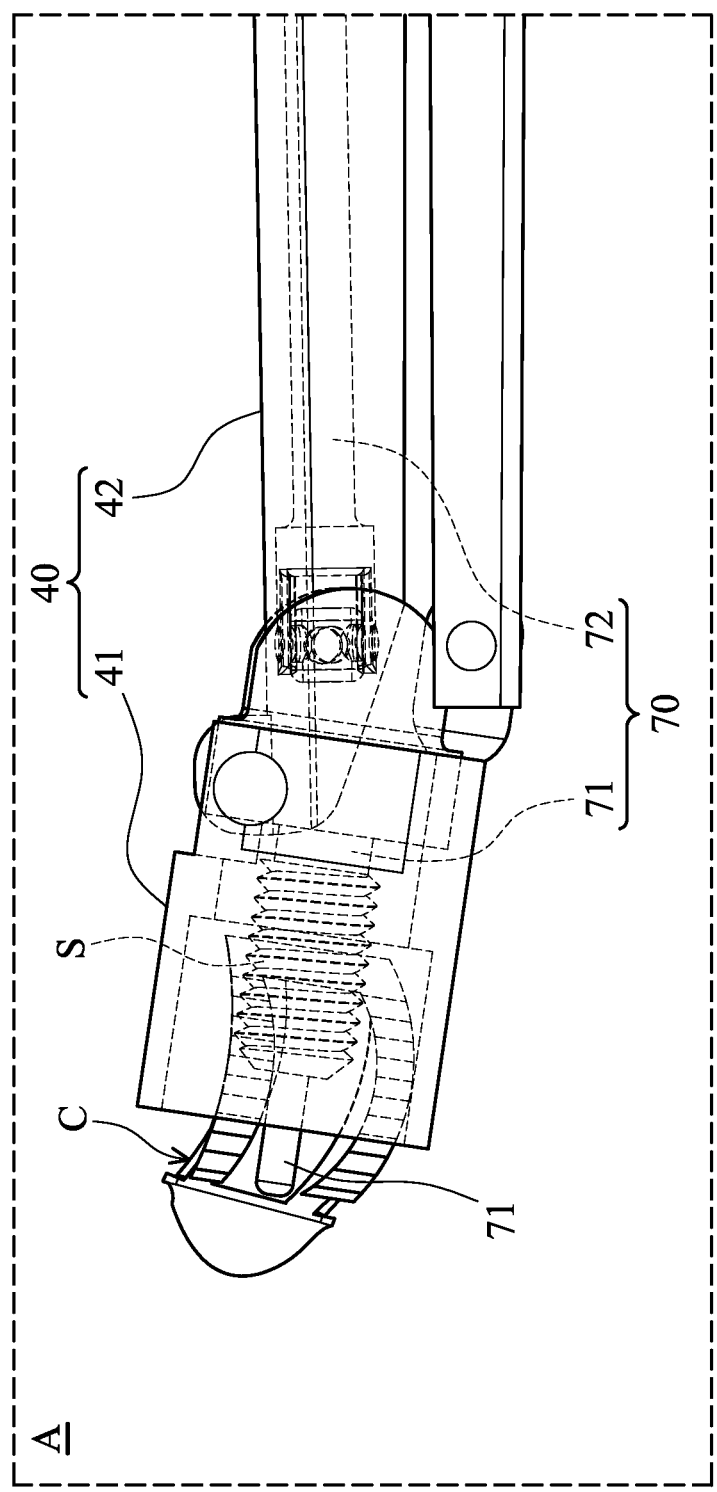
Figure 9A:
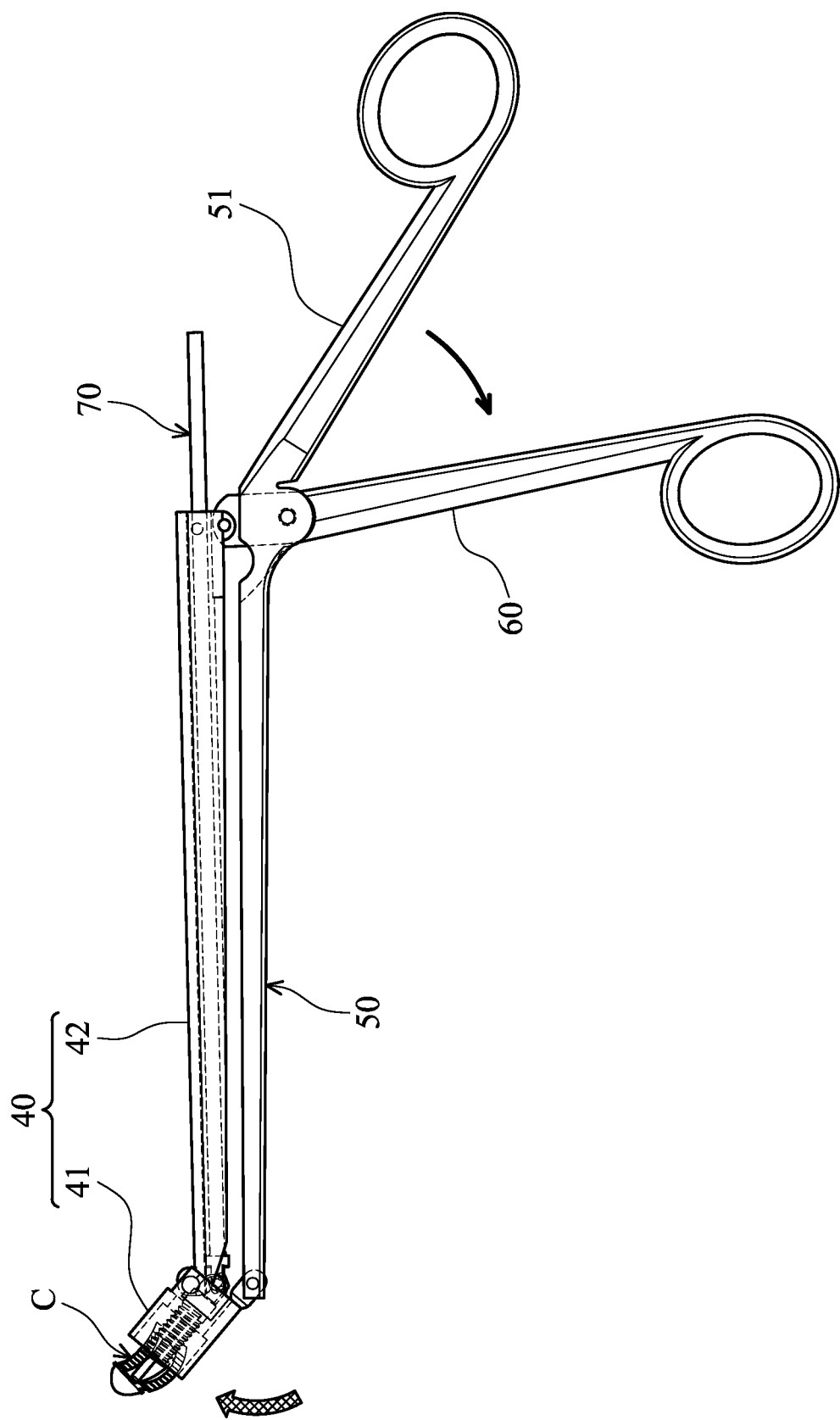
FIG. 9a is a perspective diagram of a spinal cage lifting up according to an embodiment of the disclosure.

Referring to FIGS. 8a and 8b, the spinal cage C is disposed in the first tube 41 before implanting, and a pushing mechanism 70 is disposed through the hollow mechanism 40 with a threaded portion S thereof engaged with the spinal cage C (FIG. 8b). Subsequently, the spinal cage C can be implanted into the intervertebral disc space by manipulating the guiding device with the pushing mechanism 70. Since the angle between the first and second tubes 41 and 42 is adjustable by manually controlling the handle 60 and a grip 51 of the arm 50, the elevating angle of the spinal cage C can be modified during implanting, as the arrow indicates in FIG. 9a.

Figure 9B:
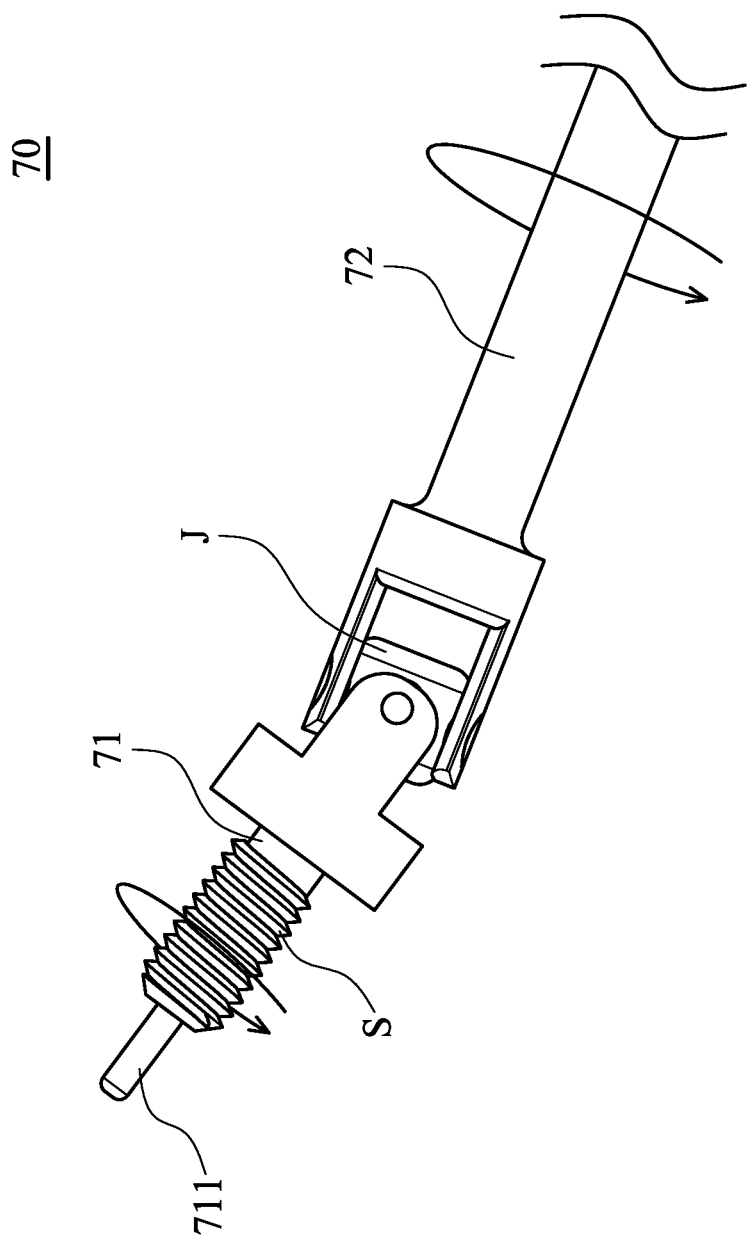
FIG. 9b is a perspective diagram of a pushing mechanism according to an embodiment of the disclosure.

FIG. 9b illustrates an embodiment of the pushing mechanism 70 which comprises a first section 71 and a second section 72 pivotally connected to each other via a universal joint J. When the second section 72 rotates axially, as the arrows indicate in FIG. 9a, the first section 71 is driven and rotated axially through the universal joint J.

Figure 10A:
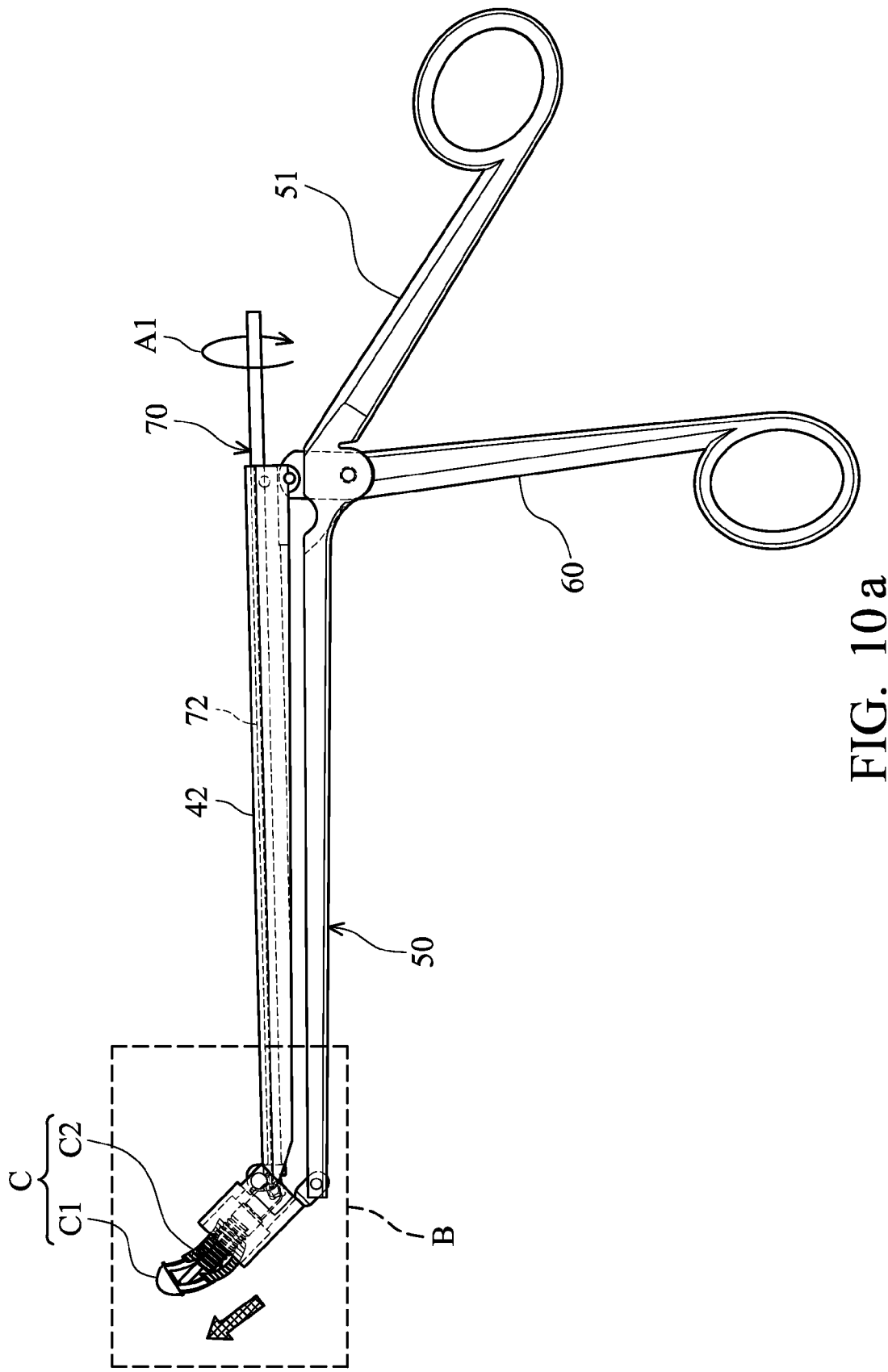
FIG. 10a is a perspective diagram of a pushing mechanism rotating along a first direction according to an embodiment of the disclosure.
Figure 10B:
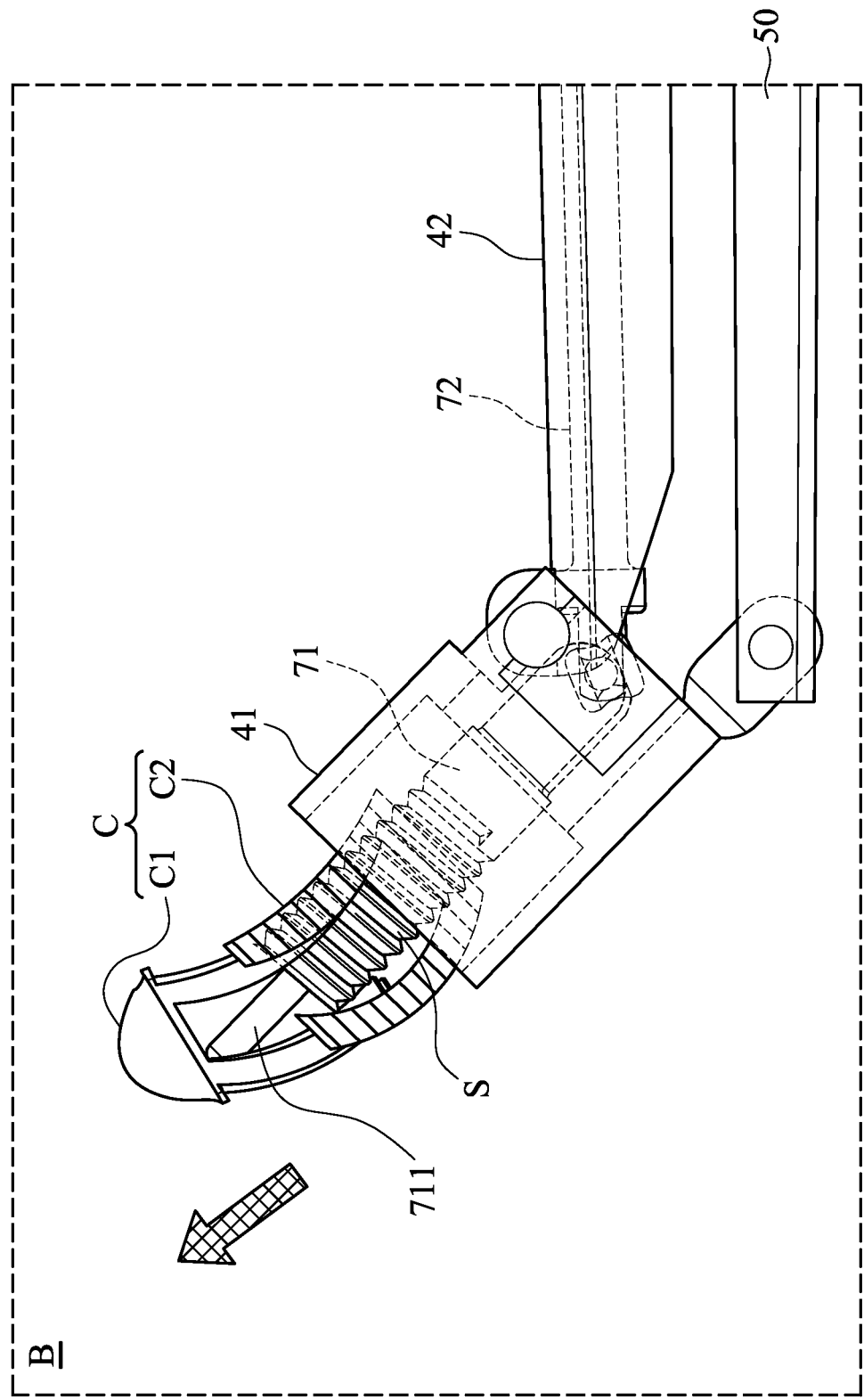

Referring to FIGS. 10a and 10b, when the spinal cage C is implanted into the intervertebral disc space, the pushing mechanism 70 can be manually rotated along a first direction A1 to screw the threaded portion S further into the spinal cage C. Meanwhile, the first segment C1 of the spinal cage C is pushed outward by a protrusion 711 extended from the threaded portion S, as shown in FIG. 10b, such that the spinal cage C is elongated to an extended state.

Figure 11:
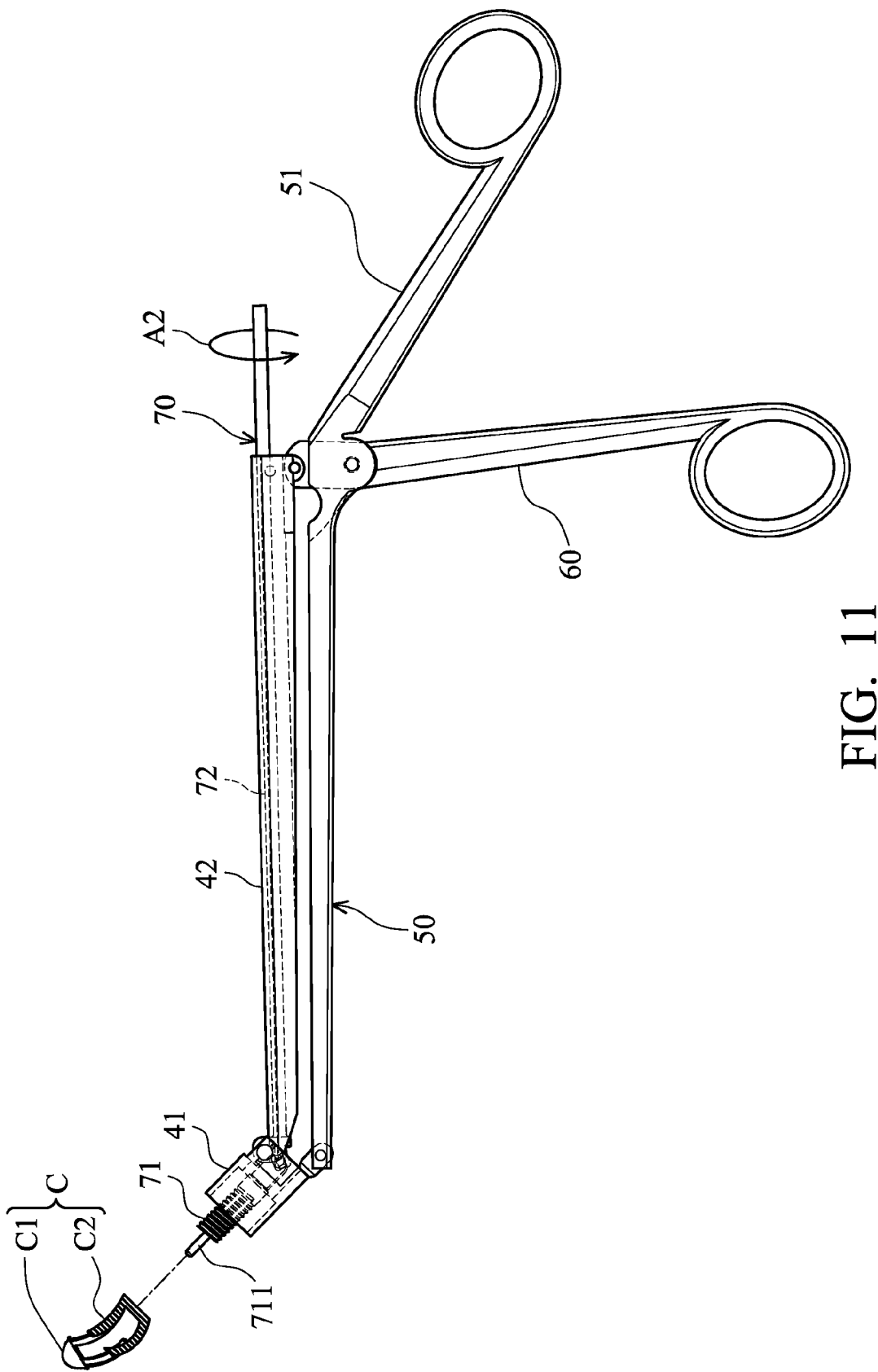
FIG. 11 is a perspective diagram of a pushing mechanism separating from a spinal cage according to an embodiment of the disclosure.

Referring to FIG. 11, after the spinal cage C elongated to the extended state, the pushing mechanism 70 is reversely rotated along a second direction A2 to separate from the second segment C2 of the spinal cage C, such that the spinal cage C is detained in the intervertebral disc. Finally, the guiding device and the pushing mechanism 70 are drawn out of the intervertebral disc to complete the implanting procedure.

Figure 12:
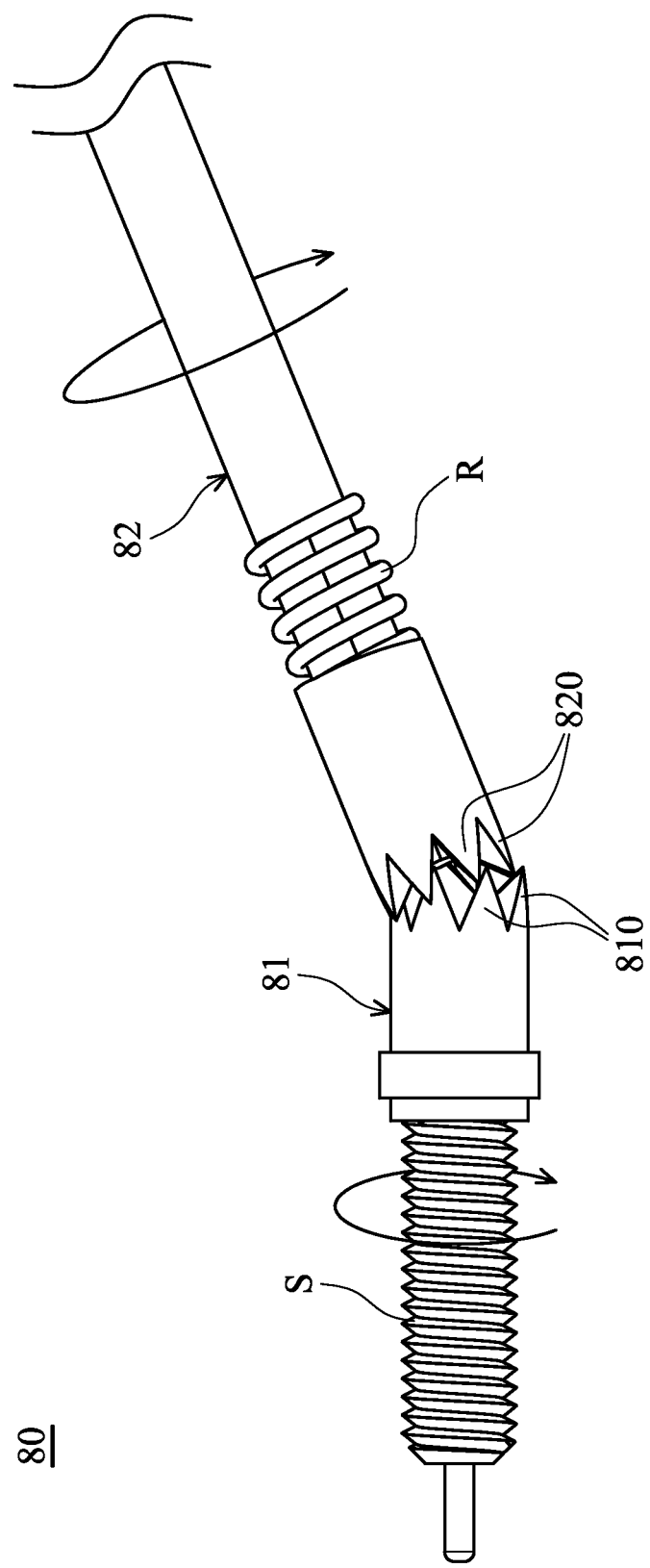
FIG. 12 is a perspective diagram of a pushing mechanism according to another embodiment of the disclosure.

The pushing mechanism 70 in FIG. 9b can be replaced by the pushing mechanism 80 in FIG. 12. The pushing mechanism 80 of FIG. 12 comprises a first section 81 and a second section 82, wherein the first section 81 has a plurality of first teeth 810, and the second section 82 has a plurality of second teeth 820 movably engaged with the first teeth 810. When the second section 82 rotates axially, the second teeth 820 slide between the first teeth 810, and the first section 81 is driven and rotated axially by the second section 82, as the arrows indicate in FIG. 12. In this embodiment, the first and second sections 81 and 82 may be connected by a rope or metal wire received therein to prevent separation thereof. Additionally, the pushing mechanism 80 further comprises a spring R disposed on the second section 82 to absorb shock when the second teeth 820 slide between the first teeth 810.

Figure 13:
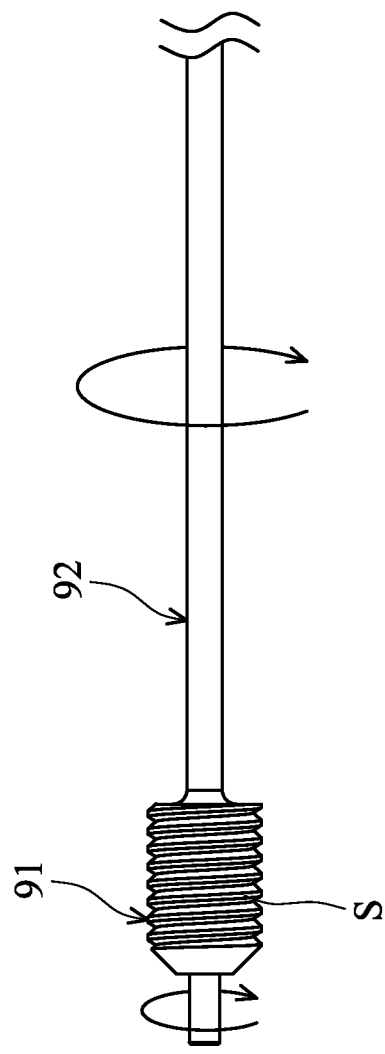
FIG. 13 is a perspective diagram of a pushing mechanism according to another embodiment of the disclosure.

The pushing mechanism 70 in FIG. 9b may also be replaced by the pushing mechanism 90 in FIG. 13. In this embodiment, the pushing mechanism 90 comprises a first section 91 and a second section 92. The second section 92 may be a flexible and elongated metal bar. When the second section 92 rotates axially, the first section 91 is driven and rotated axially by the second section 92, as the arrows indicate in FIG. 13. Since the second section 92 is flexible, the angle between the first and second tubes 41 and 42 will not obstruct operation of the pushing mechanism 90.

The disclosure provides an extendable spinal cage and an implanting method thereof. The spinal cage is retracted before being implanted into the human body. Specifically, the spinal cage can be elongated to an extended state by auxiliary appliances to provide robust support and connection between the vertebrae. The extendable spinal cage of the invention is easy to position and suitable for minimally invasive surgery, thus improving safety and saving time and cost of surgical operations.

While the disclosure has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation to encompass all such modifications and similar arrangements.

What is claimed is:

1. A method comprising:
   providing a spinal cage comprising a first segment and a second segment movable with respect to the first segment;
   providing a pipe and inserting the pipe into an intervertebral disc space of a human body;
   delivering the spinal cage through the pipe to the intervertebral disc space using a tube which is directly connected to the spinal cage, wherein the second segment has a threaded portion at an end thereof detachably connected to the tube;
   inserting a rod into the tube and pushing the first segment therewith to drive the first segment to slide with respect to the second segment while the spinal cage is connected to the tube; and
   drawing the rod, the tube, and the pipe out of the human body sequentially and leaving the spinal cage in the intervertebral disc space.

2. The method as claimed in claim 1, further comprising: delivering filler through the tube to the first segment by the rod.

3. The method as claimed in claim 2, wherein the filler comprises autologous tissue, allograft tissue, or artificial bone substitute.

4. The method as claimed in claim 3, wherein the filler comprises porous material.

5. The method as claimed in claim 3, wherein the filler comprises hydroxyapatite (HAp), tricalcium phosphate, CaSO4, CaCO3, collagen, or gelatin.

6. The method as claimed in claim 1, further comprising: delivering filler through the tube to the second segment by the rod.

7. The method as claimed in claim 1, further comprising: adjusting the spinal cage to a target position in the intervertebral disc space by moving the tube.

8. The method as claimed in claim 1, wherein the first and second segments are curved and hollow.

9. The method as claimed in claim 1, wherein the spinal cage is in a retracted state when delivered to the intervertebral disc space, and is extended into an extended state when the first segment is pushed by the rod to slide with respect to the second segment.

* * * * *